US010709443B2

(12) United States Patent
Anderson et al.

(10) Patent No.: US 10,709,443 B2
(45) Date of Patent: Jul. 14, 2020

(54) DEVICES AND METHODS FOR SUTURE PLACEMENT

(71) Applicant: Dura Tap LLC, Wayne, PA (US)

(72) Inventors: David Greg Anderson, Villanova, PA (US); Mark F. Kurd, Wayne, PA (US); Jay Tapper, Wayne, PA (US); Jens Johnson, Austin, TX (US)

(73) Assignee: Durastat LLC, Wayne, PA (US)

( * ) Notice: Subject to any disclaimer, the term of this patent is extended or adjusted under 35 U.S.C. 154(b) by 146 days.

(21) Appl. No.: 15/909,408

(22) Filed: Mar. 1, 2018

(65) Prior Publication Data

US 2019/0269401 A1   Sep. 5, 2019

(51) Int. Cl.
*A61B 17/06*  (2006.01)

(52) U.S. Cl.
CPC .. *A61B 17/06066* (2013.01); *A61B 17/06061* (2013.01); *A61B 2017/0608* (2013.01); *A61B 2017/06052* (2013.01)

(58) Field of Classification Search
CPC .......... A61B 2017/06052; A61B 2017/00349; A61B 2017/0608
See application file for complete search history.

(56) References Cited

U.S. PATENT DOCUMENTS

| | | | | |
|---|---|---|---|---|
| 5,387,221 | A | * | 2/1995 | Bisgaard ............ A61B 17/0469 112/169 |
| 5,591,179 | A | * | 1/1997 | Edelstein ........... A61B 17/0482 |
| 5,713,910 | A | * | 2/1998 | Gordon .............. A61B 17/0469 112/169 |
| 5,741,277 | A | | 4/1998 | Gordon |
| 7,442,198 | B2 | * | 10/2008 | Gellman ............ A61B 17/0469 606/139 |
| 7,993,354 | B1 | | 8/2011 | Brecher |
| 2005/0251210 | A1 | | 11/2005 | Westra |
| 2009/0024145 | A1 | | 1/2009 | Meade |

(Continued)

FOREIGN PATENT DOCUMENTS

WO     2017/136022     8/2017

OTHER PUBLICATIONS

International Search Report filed in PCT/US19/19477 dated May 15, 2019.

(Continued)

*Primary Examiner* — Gregory A Anderson
*Assistant Examiner* — Alyssa M Keane
(74) *Attorney, Agent, or Firm* — Rankin, Hill & Clark LLP

(57) ABSTRACT

A suturing device includes a needle, a suture, an elongate body, an actuator and a curved needle holder. The needle has first end, which is pointed, a second end, a curved distal section and a straighter proximal section, which is straight or has a radius of curvature greater than the curved distal section. The suture connects with the needle. The actuator includes a mechanism operable to move the needle with respect to the elongate body. The curved needle holder extends away from a distal end portion or is provided as part of the distal end portion of the elongate body. The curved needle holder includes an inner surface defining a curved needle passage for holding the needle and a distal opening through which the needle exits the curved needle holder. The needle frictionally engages the inner surface when the needle is in a retracted position.

18 Claims, 5 Drawing Sheets

(56) References Cited

U.S. PATENT DOCUMENTS

2014/0222033 A1*  8/2014  Foerster ............. A61B 17/0469
                                                                606/144
2014/0296880 A1   10/2014  Heneveld
2017/0020511 A1*  1/2017  Roorda .............. A61B 17/0482
2018/0221019 A1*  8/2018  Underdown ..... A61B 17/06066

OTHER PUBLICATIONS

International Search Report filed in PCT/US2018/042652 dated Oct. 11, 2018.

* cited by examiner

DEVICES AND METHODS FOR SUTURE PLACEMENT

BACKGROUND

The present disclosure relates generally to surgery and the placement of sutures, and more particularly, to devices and methods for the suture repair of tissue.

Surgical closure techniques using a needle to pass a suture is one approach to tissue repair. Maintaining the needle within the device that is used to deploy the needle through the tissue can present challenges.

SUMMARY

In view of the foregoing, a suturing device includes a needle, a suture, an elongate body, an actuator and a curved needle holder. The needle has first end, which is pointed, a second end, a curved distal section and a straighter proximal section, which is straight or has a radius of curvature greater than the curved distal section. The suture connects with the needle. The elongate body includes a proximal end portion and a distal end portion. The actuator includes a mechanism operable to move the needle with respect to the elongate body. The curved needle holder extends away from the distal end portion or is provided as part of the distal end portion of the elongate body. The curved needle holder includes an inner surface defining a curved needle passage for holding the needle and a distal opening through which the needle exits the curved needle holder when moving from a retracted position toward a released condition. The needle frictionally engages the inner surface when the needle is in the retracted position.

DETAILED DESCRIPTION

Figure 1:
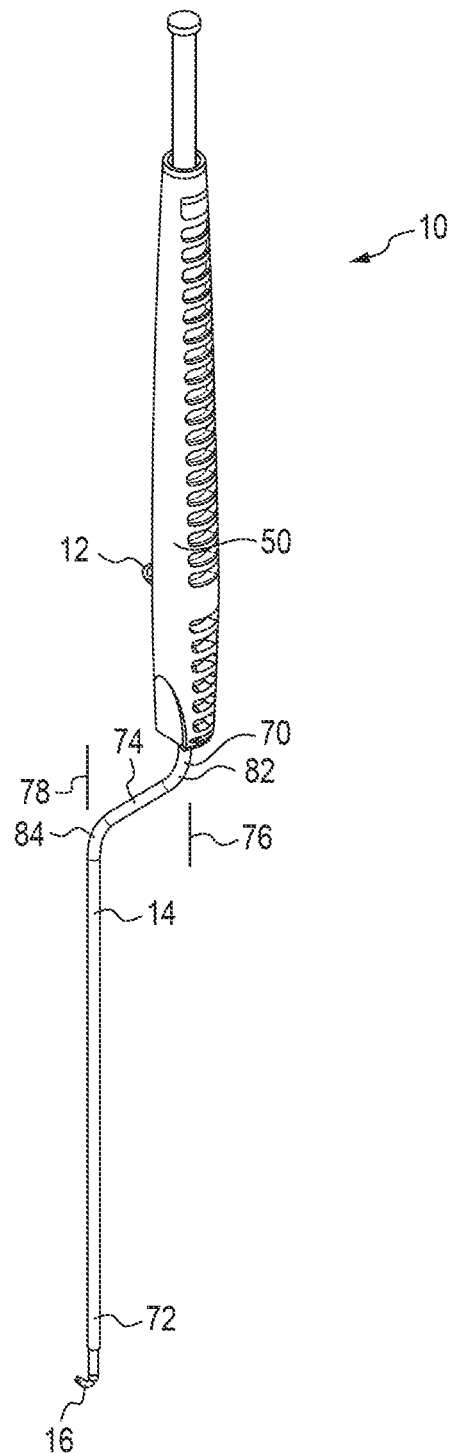
FIG. 1 is a perspective view a suturing device.
Figure 2:
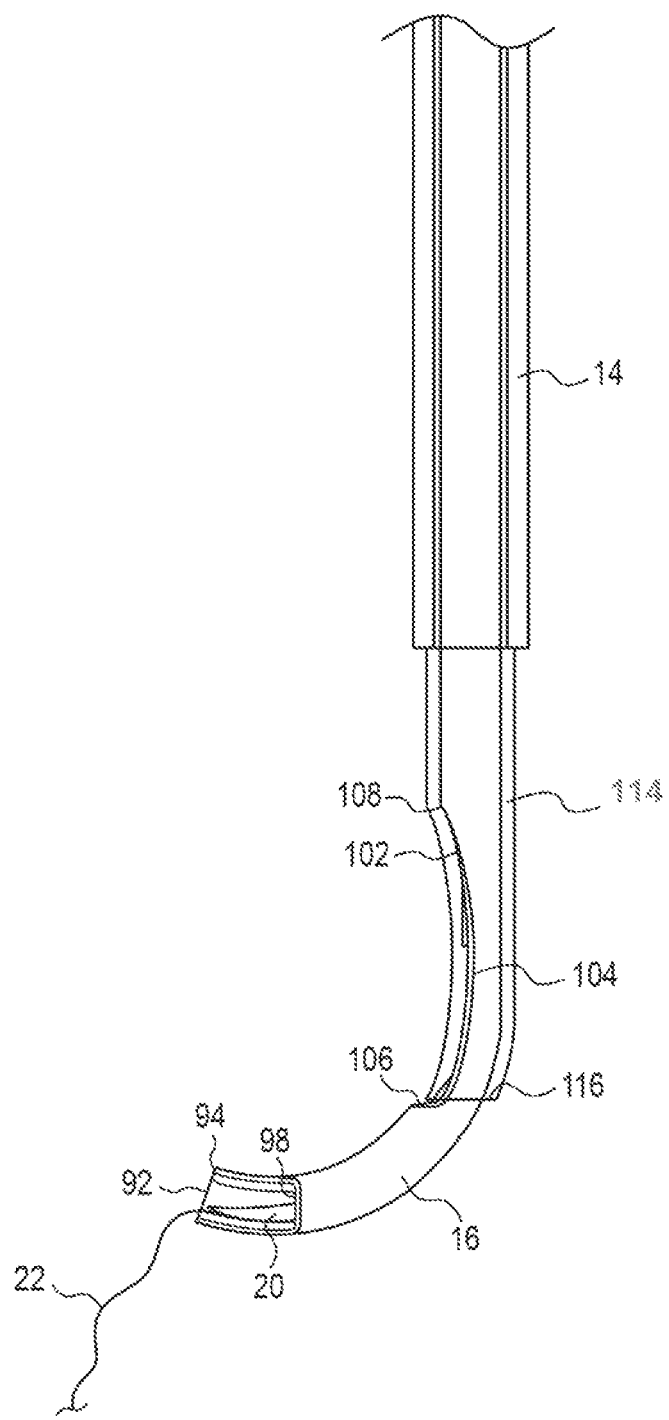
FIG. 2 is a side view of a distal portion of the suturing device of FIG. 1.

FIG. 1 depicts an example of a suturing device 10 that is useful to suture tears in tissue and that can be used in many different types of surgical procedures. The suturing device 10 generally includes an actuator button 12, an elongate body 14, and a needle holder 16. The suturing device 10 is particularly useful during a minimally invasive surgical procedure that is performed through a tubular retractor or other small surgical portal to accurately locate a needle 20 and a suture 22, which are shown in FIG. 2, to facilitate passing the needle 20 through target tissue to be sutured.

Figure 3:
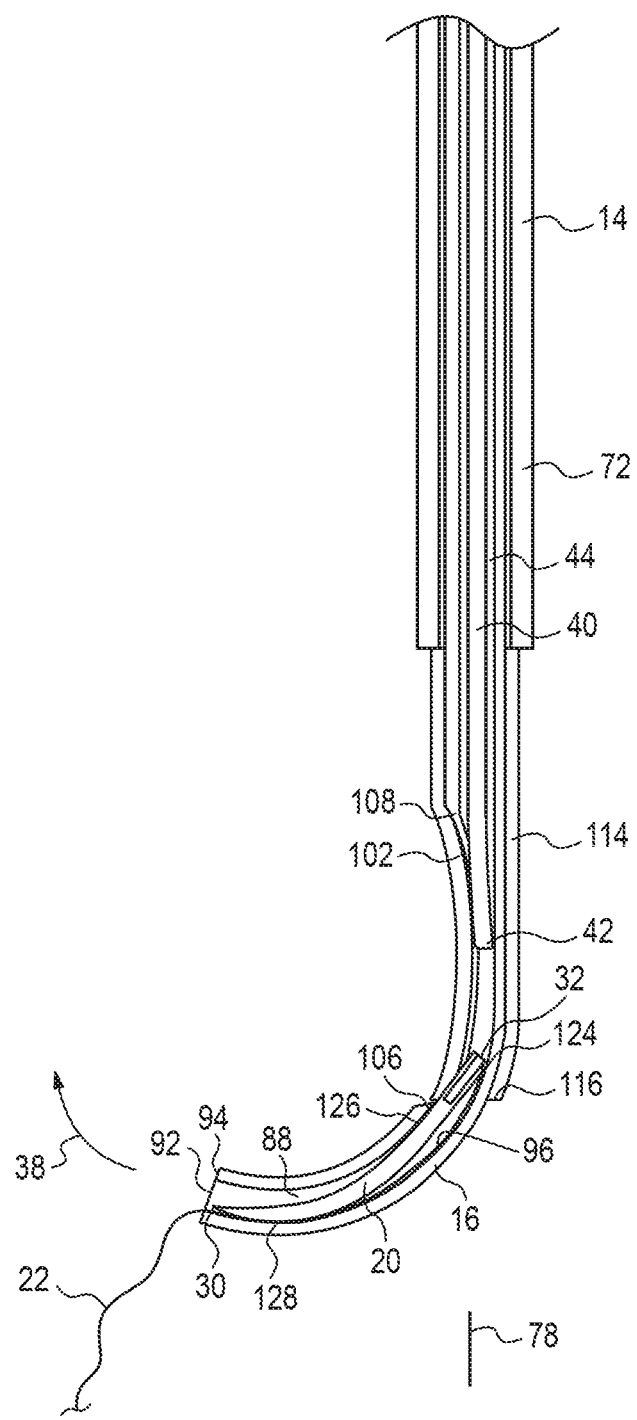
FIG. 3 is a cross-sectional view of the distal portion of the suturing device of FIG. 1.
Figure 4:
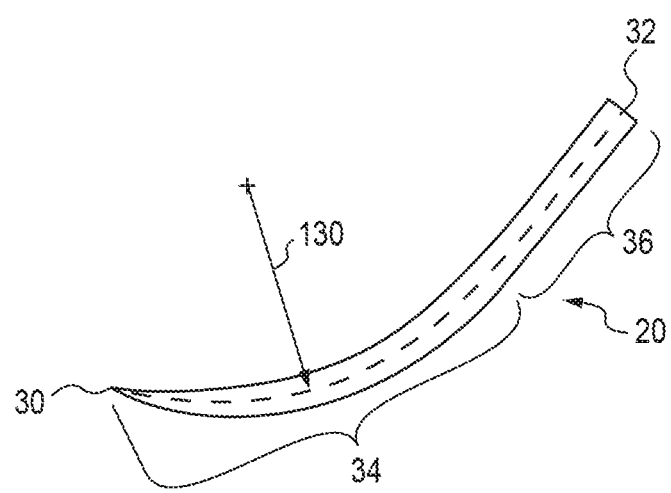
FIG. 4 is a side view of a needle of the suturing device of FIG. 1.

With reference to FIG. 3, the needle 20 in the illustrated embodiment has a first end 30, which is pointed, and a second end 32, which is opposite to the first end 30. With reference to FIG. 4, the needle 20 includes a curved distal section 34 and a straighter proximal section 36. The length of the curved distal section 34 is more than one half of the overall length of the needle 20. In the illustrated embodiment, the curved distal section 34 extends from the first end 30 toward the second end 32 for about 60% of the overall length of the needle, and the straighter proximal section 36 extends from the second end 32 toward the first end 30 for about 40% of the overall length of the needle 20. The straighter proximal section 36 can extend from the second end 32 toward the first end 30 for less than 40% of the overall length of the needle 20, so long as the needle 20 frictionally engages with the needle holder 16 as described in more detail below. With continued reference to FIG. 4, straighter proximal section 36 is shown as straight in that a central axis of the straighter proximal section 36 follows a line. The straighter proximal section 36 need not be exactly straight, but instead could have a radius of curvature greater, or vastly greater, than the curved distal section 34.

With reference back to FIG. 1, the actuator button 12 is a component of an actuator that is described in more detail in U.S. application Ser. No. 15/654,878 and for the sake of brevity will not be described in detail herein. With reference to FIG. 3, actuation of the actuator button 12 results in the needle 20 moving in an advance direction 38 with respect to the needle holder 16. The needle 20 moves from a retracted position, which is shown in FIG. 3, to a released condition in which the needle 20 is released from the needle holder 16. When in the released condition, the surgeon can grasp the needle 20, for example with forceps, and pull the needle 20 and the suture 22.

The suture 22 connects with the needle 20 and extends from the second end 32 of the needle 20. The suture 22 can be acquired from known suture manufacturers. The suture 22 can be swaged to the second end 32 of the needle 20. Swaging the suture 22 to the second end 32 of the needle 20 can result in straightening of a previously curved needle to provide the straighter proximal section 36. The suture 22 can also connect with the needle 20 in other conventional manners.

The actuator, which includes the actuator button 12, is operable between a first operating position and a second operating position. Movement of the actuator from the first operating position toward the second operating position moves the needle 20 in the advance direction 38 with respect to the needle holder 16 thus moving the needle 20 toward the released condition in which the needle 20 is released from the needle holder 16. In the illustrated embodiment and with reference to FIG. 3, the actuator includes a flexible section, which in the illustrated embodiment is made up of a wire 40, which can be made from nitinol. The wire 40 includes a distal end 42 and is configured to bend within the needle holder 16 when the actuator is moved from the first operating position toward the second operating position.

With reference back to FIG. 1, the elongate body 14 connects with a handle 50. The elongate body 14 in the illustrated embodiment is in the form of a cannula and defines a track 44, which can be a lumen, that receives the wire 40. The elongate body 14 has a bayonet configuration in the illustrated embodiment; however, the elongate body 14 could take alternative configurations, such as straight along a longitudinal axis. The elongate body 14 includes the proximal end portion 70 and a distal end portion 72 connected by an intermediate portion 74. The proximal end portion 70 connects with the handle 50. In the illustrated embodiment, the needle holder 16 is received in and connected with the elongate body 14 and extends away from the distal end portion 72. Alternatively, the needle holder 16 can be provided as part of the distal end portion 72 of the elongate body 14. The elongate body 14 is made from a rigid metal material; however, if desired at least a portion of the elongate body 14 may be made from a malleable or flexible material. In the illustrated embodiment, an outer diameter of the elongate body 14 is constant between the proximal end portion 70 and the distal end portion 72. The outer diameter can be less than 3.5 mm, which provides a very slim device to enhance the line of sight for a surgeon during the surgical procedure. The intermediate portion 74 is positioned between the proximal end portion 70 and the distal end portion 72. The proximal end portion 70 extends along a proximal end portion longitudinal axis 76. The distal end portion 72 extends along a distal end portion longitudinal axis 78, which is offset from the proximal end portion longitudinal axis 76 in a forward direction. In the illustrated embodiment, the distal end portion longitudinal axis 78 is offset from the proximal end portion longitudinal axis 76 about 25 mm. The proximal end portion 70 transitions to the intermediate portion 74 through a proximal bend 82 and the intermediate portion 74 transitions to the distal end portion 72 through a distal bend 84. In the illustrated embodiment, the proximal bend 82 and the distal bend 84 are both angled internally 135 degrees.

The needle holder 16 extends away from the distal end portion 72 or is provided as part of the distal end portion 72 of the elongate body 14. With reference to FIG. 3, the needle holder 16 is a hollow tubular member. In the illustrated embodiment, a portion of the needle holder 16 that is aligned with the distal end portion longitudinal axis 78 is received inside the elongate body 14; however, the needle holder 16 could be formed as part of the elongate body, e.g., both the elongate body 14 and the needle holder 16 could be made from one tubular stock material. The needle holder 16 depicted in the illustrated embodiment is a curved needle holder that generally follows a constant needle passage radius 90 (FIG. 5) such that the suturing device 10 can have J-hook configuration at a distal end thereof. In the illustrated embodiment, the needle holder 16 is not intended to be removable from the elongate body 14; however, in an alternative arrangement the needle holder 16 can selectively connect with the elongate body 14 via a mechanical connection such as a friction fit or a bayonet connection.

The needle holder 16 defines a needle passage 88 that follows the needle passage radius 90 and is in communication with the track 44. The needle passage 88 terminates at a distal opening 92 adjacent a distal-most tip 94 of the needle holder 16. The needle passage 88 follows an arc length less than about 140 degrees between a location where the needle holder 16 begins to curve away from the distal end portion longitudinal axis 78 and the distal-most tip 94. The distal opening 92 is offset from the distal end portion longitudinal axis 78 in a forward direction. In the embodiment depicted in FIG. 3, at least a portion of the suture 22 extends along the needle passage 88 from the second end 32 of the needle 20 toward the distal opening 92 between the needle 20 and an inner surface 96 of the needle holder 16 when the needle 20 is received in the needle passage 88 and in the retracted position. The distal-most tip 94 is offset from the distal end portion longitudinal axis 78 in a direction perpendicular from the distal end portion longitudinal axis 78 a distance of less than 7 mm. Common tubular retractors used during minimally invasive spinal surgery procedures have diameters measuring between 14 mm to 22 mm. By spacing the distal-most tip 94 offset from the distal end portion longitudinal axis 78 less than 7 mm, the surgeon can locate the elongate body 14 along the central axis of the tubular retractor and rotate the suturing device around the central axis without contacting the side of the tubular retractor.

As more clearly seen in FIG. 2, the needle holder 16 includes a distal notch 98 at the distal opening 92 adjacent the distal-most tip 94. The distal notch 98 extends in a proximal direction toward the elongate body 14. By providing the distal notch 98, the second end 32 of the needle 20 need not travel past the distal-most tip 94 of the needle holder 16 before being released from the needle holder 16. Such a configuration of the distal opening 92 also facilitates loading of the needle 20 and the suture 22 into the needle passage 88, which occurs by inserting the second end 32 of the needle 20 into the distal opening 92 and moving the needle 20 with respect to the needle holder 16 in a direction opposite to the advance direction 38. The configuration of the distal opening 92 also reduces the likelihood that the first end 30 of the needle 20 may pass through the suture 22 when being passed through the target tissue. The distal notch 98 is depicted on the side of the needle holder 16, however, the distal notch 98 can be located elsewhere. By providing the distal notch 98, the distal opening 92 is non-circular. The distal-most tip 94 can also be rounded, which allows for the surgeon to grab or "hook" the target tissue, which is to be sutured, on an internal side thereof and indent the target tissue with the distal-most tip 94 while not catching the target tissue with the first (pointed) end 30 of the needle 20.

The needle holder 16 also includes a proximal hole 102 defined by a peripheral edge 104 and spaced from the distal opening 92. In a side view, the proximal hole 102 is elongated along the distal end portion longitudinal axis 78. In the illustrated embodiment, the proximal hole 102 extends through an inner side of the needle holder 16 in that the proximal hole 102 is located through a side of the needle holder 16 nearest to the center of the needle passage radius 90. A lower end 106 of the proximal hole 102 is located near where the second end 32 of the needle 20 resides when the needle 20 in the retracted position. An upper end 108 of the proximal hole 102 is located above (i.e., toward the handle 50) from the distal end 42 of the wire 40.

A needle retainer can be provided to retain the needle 20 within the needle passage 88 to inhibit unintended movement of the needle 20 with respect to the needle holder 16. One example of such a needle retainer is a flexible sheath 114 that is shown as transparent in FIG. 2. The flexible sheath 114 surrounds the needle holder 16 and terminates at a lower end 116, which is located adjacent the lower end 106 of the proximal hole 102. The flexible sheath 114 extends into the proximal hole 102 to retain the second end 32 of the needle 20 against the inner surface 96 of the needle holder 16 when the needle 20 is received in the needle passage 88 in the retracted position. An entirety of the flexible sheath 114 can be made from a resilient material, or the portion of the flexible sheath 114 that extends into the needle passage 88 through the proximal hole 102 may be made from the resilient material.

The flexible sheath 114 can conform to the peripheral edge 104 of the proximal hole 102 and urge the distal end 42 of the wire 40 and the second end 32 of the needle 20 toward an outer side of the inner surface 96 of the needle holder 16, i.e., the side of the inner surface 96 spaced farthest from the center of the needle passage radius 90. The flexible sheath 114 effectively reduces the cross section, or inner diameter, of the track 44 and the needle passage 88 and acts to guide the distal end 42 of the wire 40 toward the second end 32 of the needle 20 when the distal end 42 is moved toward the needle 20. When the actuator is moved from the first operating position to the second operating position, the wire 40 in the illustrated embodiment presses against the second end 32 of the needle 20 overcoming the retaining force of the flexible sheath 114 and moves the needle 20 in the advance direction 38.

Figure 5:
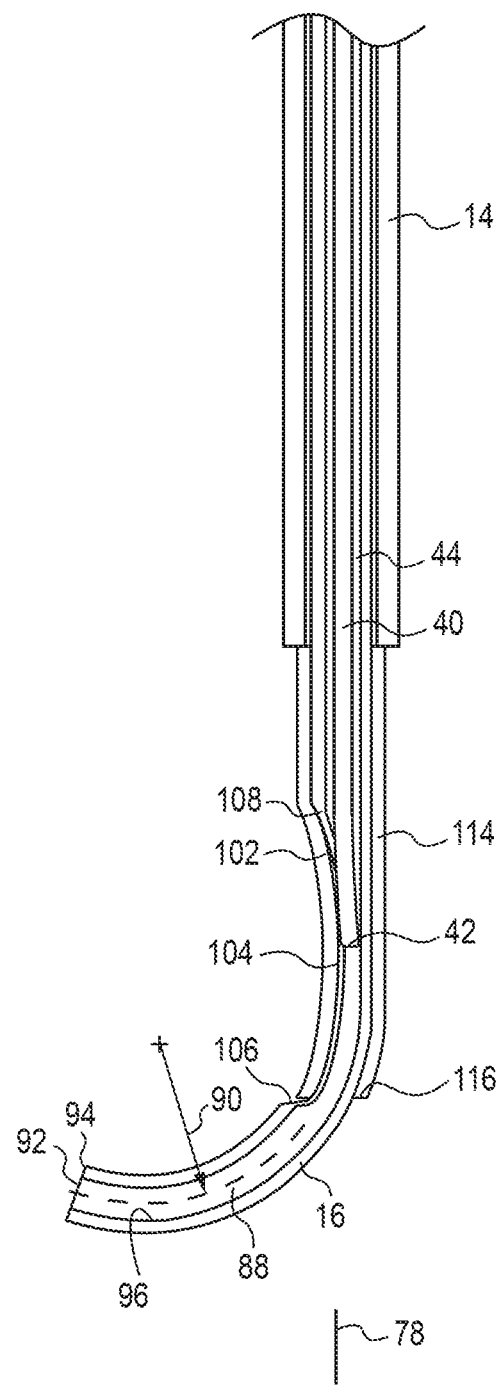
FIG. 5 is another cross-sectional view of the distal portion of the suturing device of FIG. 1 with the needle and suture removed.

When the needle 20 is in the retracted position, the needle 20 is in contact with the inner surface 96 of the needle holder 16 to inhibit unintended movement of the needle 20 with respect to the needle holder 16. The needle 20 contacts the inner surface 96 in at least three different locations along the length, or arc length, of the needle 20, e.g., a first location 124, a second location 126 and a third location 128, which are depicted in FIG. 3. The first location 124 is located adjacent to the second end 32 of the needle 20. The second location 166 is located offset of the second end 32 and toward the first end 30 of the needle 20. The third location 168 is located offset of the first end 30 and toward the second end 32 of the needle 20. The first location 124 and the third location 128 are located on an outer surface of the needle 20, i.e. the surface of the needle 20 spaced farthest from the center of the needle passage radius 90 (FIG. 5). The second location 126 is along an inner surface of the needle 20 with respect to the center of the needle passage radius 90. The first location 124 and the second location 126 are located along the straighter proximal section 36 (FIG. 4) of the needle 20, and the third location 128 is located along the curved distal section 34 of the needle 20.

Providing the needle 20 with the curved distal section 34, which can have a curved needle radius 130 (FIG. 4) similar to the needle passage radius 90, and with the straighter proximal section 36 results in the needle 20 being wedged into the needle holder 16. The three contact locations 124, 126, 128 keep the needle 20 retained and stable in the retracted position until the needle 20 is pushed by the wire 40. For example, the curved distal section 34 can have a curved needle radius 130 of 3.4 mm and the needle passage radius 90 can be 4.0 mm, which results in the curved needle radius 130 being about 85% of the needle passage radius 90. Also, the straighter proximal section 36 extends from the second end 32 long enough, which may or may not be at least about 40% of the overall length of the needle 20, so that the needle 20 frictionally engages the inner surface 96 of the needle holder 16. Also, the needle 20 can have a maximum outer diameter that is at least 40% of the inner diameter of the needle passage 88, which can facilitate retaining the needle 20 within the needle passage 88. Also, the needle 20 can have an outer diameter that is not greater than 90% of the inner diameter of the needle passage 88, which can allow the needle passage 88 to accommodate both the needle 20 and the suture 22.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A suturing device comprising:
   a needle having first end, which is pointed, and a second end, the needle having a curved distal section and a straighter proximal section, which is straight or has a radius of curvature greater than the curved distal section;
   a suture connected with the needle;
   an elongate body including a proximal end portion and a distal end portion;
   an actuator including a mechanism operable to move the needle with respect to the elongate body;
   a curved needle holder extending away from the distal end portion or provided as part of the distal end portion of the elongate body, the curved needle holder including an inner surface defining a curved needle passage for holding the needle and a distal opening through which the needle exits the curved needle holder when moving from a retracted position toward a released condition; and
   wherein the needle frictionally engages the inner surface in a least three different locations along the needle when the needle is in the retracted position.

2. The suturing device of claim 1, wherein a length of the straighter proximal section is a minority of an overall length of the needle.

3. The suturing device of claim 2, wherein the length of the straighter proximal section of the needle is at least 20% of the overall length of the needle.

4. The suturing device of claim 2, wherein the length of the straighter proximal section of the needle is at least 40% of the overall length of the needle.

5. The suturing device of claim 1, wherein the needle contacts the inner surface of the curved needle holder at a first location, a second location and a third location along the needle, wherein the first location is located adjacent to the second end, wherein the second location is located offset from the second end toward the first end, and wherein the third location is located offset from the first end toward the second end.

6. The suturing device of claim 5, wherein the first location and the third location are located on an outer surface of the needle and the second location is along an inner surface of the needle, the outer surface and the inner surface of the needle being positioned with respect to a center of a radius of curvature for the curved needle passage.

7. The suturing device of claim 1, wherein the first end of the needle is offset from the inner surface of the curved needle passage at a distal-most tip of the needle holder when the needle is in the retracted position.

8. The suturing device of claim 1, wherein the curved needle passage follows an arc length less than 140 degrees between a location where the curved needle holder begins to curve away from a longitudinal axis of the suturing device and a distal-most tip of the needle holder.

9. The suturing device of claim 1, wherein the curved needle holder includes a distal notch at the distal opening that extends in a proximal direction toward the elongate body.

10. A suturing device comprising:
    a needle having first end, which is pointed, and a second end, the needle having a curved distal section and a straighter proximal section, which is straight or has a radius of curvature greater than the curved distal section;
    a suture connected with the needle;
    an elongate body including a proximal end portion and a distal end portion;
    an actuator including a mechanism operable to move the needle with respect to the elongate body;
    a curved needle holder extending away from the distal end portion or provided as part of the distal end portion of the elongate body, the curved needle holder including an inner surface defining a curved needle passage for holding the needle and a distal opening through which the needle exits the curved needle holder when moving from a retracted position toward a released condition; and
    wherein the needle frictionally engages the inner surface when the needle is in the retracted position, wherein at least a portion of the suture extends along the curved needle passage from the second end of the needle toward the distal opening between the needle and the inner surface of the curved needle holder when the needle is received in the curved needle passage in the retracted position.

11. A suturing device comprising:

a needle having first end, which is pointed, and a second end, the needle having a curved distal section and a straighter proximal section, which is straight or has a radius of curvature greater than the curved distal section;

a suture connected with the needle;

an elongate body including a proximal end portion and a distal end portion;

an actuator including a mechanism operable to move the needle with respect to the elongate body;

a curved needle holder extending away from the distal end portion or provided as part of the distal end portion of the elongate body, the curved needle holder including an inner surface defining a curved needle passage for holding the needle and a distal opening through which the needle exits the curved needle holder when moving from a retracted position toward a released condition, the curved needle holder including a proximal hole extending into the curved needle passage, wherein the proximal hole is spaced from the distal opening; and a needle retainer engaging the needle holder and the needle when the needle is in the retracted position and configured to inhibit movement of the needle toward distal opening, wherein a portion of the needle retainer extends into the curved needle passage through the proximal hole when the needle is in the retracted position, wherein the needle frictionally engages the inner surface when the needle is in the retracted position.

12. The suturing device of claim 11, wherein the portion of the needle retainer extending into the curved needle passage through the proximal hole is made from a resilient material.

13. The suturing device of claim 11, wherein an entirety of the needle retainer is made from the resilient material.

14. The suturing device of claim 11, wherein the needle retainer is a flexible sheath that surrounds the needle holder and terminates at a lower end, which extends into the proximal hole.

15. The suturing device of claim 11, wherein the needle retainer is a flexible sheath that surrounds the needle holder, conforms to a peripheral edge of the proximal hole and extends into the proximal hole.

16. The suturing device of claim 15, wherein the needle moves from the retracted position toward the released condition as the actuator moves from a first operating position toward a second operating position, wherein the actuator includes a wire and the proximal hole extends into the curved needle passage where a distal end of the wire resides when the actuator is in the first operating position.

17. The suturing device of claim 16, wherein the flexible sheath urges the wire and the second end of the needle in the same direction against the inner surface of the curved needle passage.

18. The suturing device of claim 16, wherein the flexible sheath urges the wire and the second end of the needle toward a side of the inner surface of the curved needle passage that is spaced farthest from a center of a radius of curvature for the curved needle passage.

* * * * *